(12) United States Patent
Olsson et al.

(10) Patent No.: US 6,831,679 B1
(45) Date of Patent: Dec. 14, 2004

(54) VIDEO CAMERA HEAD WITH THERMAL FEEDBACK LIGHTING CONTROL

(75) Inventors: Mark S. Olsson, San Diego, CA (US); Jan Soukup, San Diego, CA (US)

(73) Assignee: Deepsea Power & Light Company, San Diego, CA (US)

( * ) Notice: Subject to any disclaimer, the term of this patent is extended or adjusted under 35 U.S.C. 154(b) by 0 days.

(21) Appl. No.: 09/506,181

(22) Filed: Feb. 17, 2000

(51) Int. Cl.[7] .......................... H04N 7/18; H04N 9/47; H04N 5/217; H04N 5/225
(52) U.S. Cl. .................... 348/84; 348/241; 348/374
(58) Field of Search ..................... 348/241, 71, 73, 348/81, 372, 373, 374, 375, 376, 244, 65, 68, 75, 82, 83, 84, 85, 131, 69, 70, 370; 356/241.1, 241.3, 241.4, 241.5; 235/462.42, 435; 358/475; 600/109, 160, 169, 180

(56) References Cited

U.S. PATENT DOCUMENTS

| | | | | |
|---|---|---|---|---|
| 5,195,392 A | * | 3/1993 | Moore et al. ............... | 73/866.5 |
| 5,349,172 A | * | 9/1994 | Roustaei ................. | 235/462.42 |
| 5,508,740 A | * | 4/1996 | Miyaguchi et al. .......... | 348/244 |
| 5,754,220 A | * | 5/1998 | Smalser, Sr. .................. | 348/84 |
| 5,790,185 A | * | 8/1998 | Auzerais et al. .............. | 348/84 |
| 5,903,306 A | * | 5/1999 | Heckendorn et al. .......... | 348/85 |
| 6,111,739 A | * | 8/2000 | Wu et al. .................... | 361/106 |
| 6,229,563 B1 | * | 5/2001 | Miller et al. .................. | 348/83 |
| 6,271,880 B1 | * | 8/2001 | Kameshima et al. ........ | 348/244 |
| 6,281,991 B1 | * | 8/2001 | Mori et al. .................. | 358/475 |
| 6,741,286 B2 | * | 5/2004 | Meek et al. ................. | 348/370 |
| 6,752,951 B2 | * | 6/2004 | Meek et al. ................. | 264/263 |
| 6,796,939 B1 | * | 9/2004 | Hirata et al. ................. | 600/179 |

* cited by examiner

*Primary Examiner*—Wendy R. Garber
*Assistant Examiner*—Justin Misleh
(74) *Attorney, Agent, or Firm*—Michael H. Jester

(57) ABSTRACT

A video camera head adapted for pipe inspection has thermal feedback control of its scene lighting in order to lower its temperature and reduce unwanted noise in the video output signal. The camera head includes a rugged cylindrical camera housing having a hollow interior. A video camera is mounted inside the housing for generating video signals of an image of an interior of a pipe received through a scratch resistant window in a forward end of the housing. The video camera has a CCD with a predetermined maximum operating temperature. A termination assembly and a socket assembly are provided for operatively coupling a video push cable to the camera housing and the video camera, respectively. A large number of LEDs are mounted in the forward end of the housing surrounding the window for illuminating the interior of the pipe. A drive circuit is connected to the LEDs for driving the LEDs with a predetermined electrical drive signal. The drive circuit includes a feedback loop to a voltage regulator for controlling the level of power dissipated by the LEDs in order to ensure that the operating temperature of the CCD does not exceed the predetermined maximum operating temperature.

15 Claims, 3 Drawing Sheets

VIDEO CAMERA HEAD WITH THERMAL FEEDBACK LIGHTING CONTROL

BACKGROUND OF THE INVENTION

The present invention relates to electro-mechanical systems for inspecting the insides of buried pipes and other conduits for defects and obstructions, and more particularly, to a video camera head having thermal feedback control of its lighting in order to reduce unwanted noise in the video output signal, avoid burning a user's fingers and prevent damage to its electronic compnents.

There are many situations where it is desirable to internally inspect long lengths of pipe which are already in place, either underground, in a building, or underwater. For example, sewer and drain pipes frequently need to be internally inspected to diagnose existing problems or to determine if there are any breaks causing leakage or obstructions impairing the free flow of waste. It is also important to internally inspect steam pipes, heat exchanger pipes, water pipes, gas pipes, electrical conduits and fiber optic conduits. Frequently, pipes which are to be internally inspected have an internal diameter of six inches or less. It is sometimes necessary to inspect several hundred feet of pipe.

Over the years, video pipe inspection systems have been developed which typically include a camera which is forced down the pipe so that its interior can be viewed on a video display. It is common to record the inspection on a video recorder ("VCR"). Conventional video pipe inspection systems include a push cable which provides an electro-mechanical connection between a rugged head enclosing and protecting the video camera and a rotatable push reel which is used to pay out cable and force the head down the pipe. The push cable must be specially constructed in order to be flexible enough to make tight turns yet rigid enough to be pushed hundreds of feet down small diameter pipe. The push cable must also incorporate electrically conductive or fiber optic cable having the proper impedance for conveying the NTSC or other video signal to the video display unit and additional power and ground conductors.

Among other factors, the noise generated by the electronic circuitry of the video camera establishes the minimum luminescence or lighting required by camera to produce a clear high resolution color image. Heretofore it has been conventional to use light emitting diodes ("LEDs") mounted in the distal end of the housing of the camera head to illuminate the interior or the pipe. In some cases as many as fifty or more LEDs are mounted in the camera head, each dissipating up to one hundred and sixty milliwatts ("mW") of power. By way of example, in a conventional camera head the video camera itself may dissipate approximately one and one-half watts of power and the plurality of LEDs that provide the required lighting may dissipate eight watts of power. Due to the close physical proximity of the LEDs and the video camera, the excess heat generated by the LEDs inevitably produces high temperatures near the image sensing device of the video camera. The sensing device of the video camera is typically a charge coupled device ("CCD"). As the temperature of the CCD increases, the resulting noise induced in the video output signal increases, typically as the square root of the temperature increase of the CCD. A point of diminishing returns is reached where the thermal noise increases dramatically. When the CCD reaches a predetermined maximum operating temperature, e.g. one hundred and sixty degrees F., the resulting thermal noise induced in the video output signal becomes excessive. If the CCD is subjected to a temperature above its predetermined maximum operating temperature for too long, the performance of the video camera can be permanently degraded. The build-up of heat can become so excessive as to actually burn a user's fingers when handling the camera head.

The ability of the camera head to dissipate heat depends not only upon its internal construction, but upon the nature of its environment, e.g. ambient temperature, humidity, whether it is surrounded by liquid or air, etc. It would therefore be desirable to provide a video camera head that could utilize maximum lighting without generating excessive heat.

SUMMARY OF THE INVENTION

The present invention provides a video camera head particularly adapted for pipe inspection having thermal feedback control of its lighting in order to lower its temperature and reduce unwanted noise in the video output signal. The camera head includes a camera housing having a hollow interior. A video camera is mounted inside the housing for generating video signals of an image of an interior of a pipe. The camera has an image sensing device with a predetermined maximum operating temperature. Mechanisms are provided for operatively coupling a video push cable to the camera housing and the video camera. At least one light emitting diode is mounted in the forward end of the housing for illuminating the interior of the pipe. A drive circuit is connected to the light emitting diode for driving the light emitting diode with a predetermined electrical drive signal. The drive circuit includes a feedback loop for controlling the level of power dissipated by the light emitting diode in order to ensure that the operating temperature of the image sensing device does not exceed the predetermined maximum operating temperature.

The present invention also provides a method of providing video images of the inside of a pipe. The method involves mounting a video camera inside a housing for generating video signals of an image of an interior of a pipe, the camera having an image sensing device with a predetermined maximum operating temperature. The method further involves operatively connecting the housing and the camera to the distal end of a video push cable and pushing the housing and video camera down the interior of the pipe by paying out the video push cable. The method further involves driving at least one light emitting diode mounted in a front end of the housing with a predetermined electrical drive signal to illuminate the interior of the pipe and controlling the level of power dissipated by the light emitting diode in order to ensure that the operating temperature of the image sensing device of the video camera does not exceed the predetermined maximum operating temperature. Finally, the method involves displaying images of the interior of the pipe generated from a video output signal conveyed from the video camera over the video push cable.

DESCRIPTION OF THE PREFERRED EMBODIMENTS

For the sake of brevity, the term "pipe" as used hereafter shall refer to any elongated generally tubular member which can be advantageously inspected internally by a video inspection system having a camera head mounted on the end of a long push cable, including drain pipes, steam pipes, heat exchanger pipes, water pipes, well pipes, environmental monitoring conduits, gas pipes, electrical conduits and fiber optic conduits. The pipe may be a single long straight segment or it may be straight segments connected by on or more turns which vary from relatively small radius (tight turns) to relative large radius (wide turns).

Figure 1:
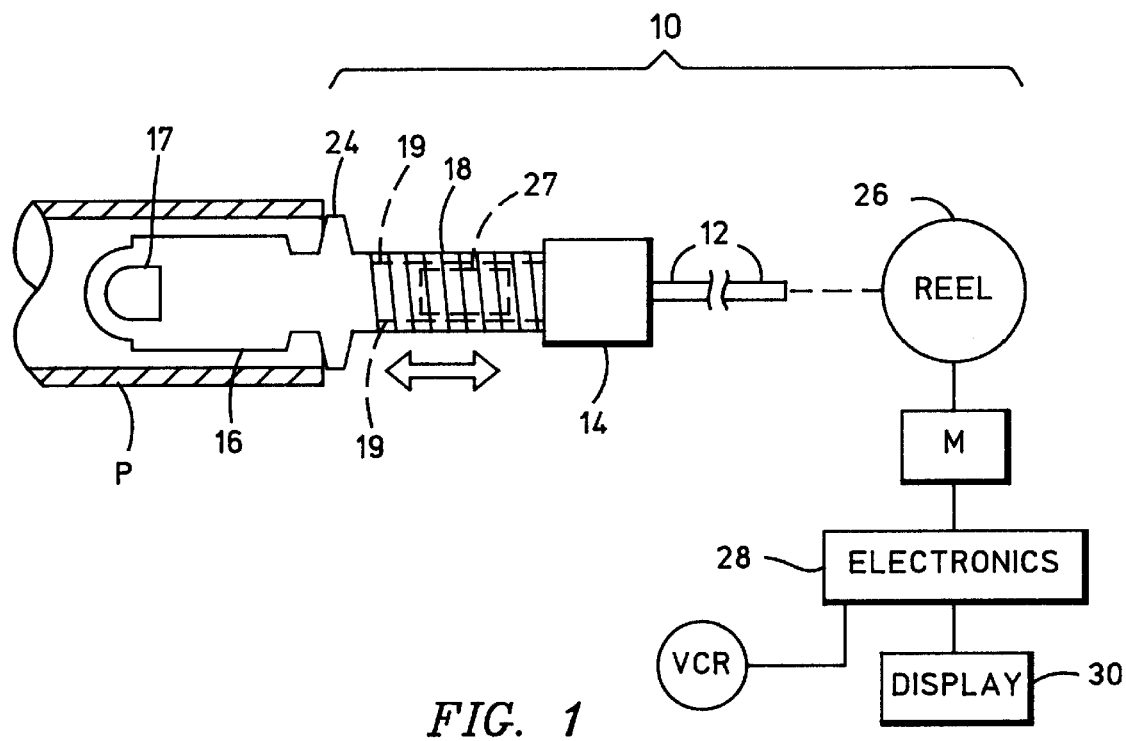
FIG. 1 is a diagrammatic illustration of a video pipe inspection system incorporating a preferred embodiment of the video camera head of the present invention.

Referring to FIG. 1, a video pipe inspection system 10 includes an elongate, resilient and flexible video push cable 12. Examples of suitable video push cables are disclosed in U.S. Pat. No. 5,457,288 granted Oct. 10, 1995 to Mark S. Olsson and U.S. Pat. No. 5,808,239 granted Sep. 15, 1998 to Mark S. Olsson, the entire disclosures of which are hereby incorporated by reference. Both patents are assigned to DeepSea Power and Light, the assignee of the subject application. The forward or distal end of the push cable 12 is operatively connected through an electro-mechanical termination assembly 14 to a video camera head 16 which includes a rugged generally cylindrical outer stainless steel housing with a hollow interior for enclosing a color video camera 17. The video camera 17 includes an optical sensing device such as a CCD. The video camera head 16 further includes a camera circuit which receives the output of the CCD and generates a video image signal representing real time images of scenes viewed by the optical sensing device through a forward end of the video camera head 16. The video camera head 16 may function with video systems employing EIA, NTSC, CCIR, PAL and other standard video signal formats. Further details of the termination assembly 14 are disclosed in the aforementioned U.S. Pat. No. 5,457,288.

A stainless steel coil spring 18 surrounds the push cable 12 and is coupled between the rear end of the video camera head 16 and the termination assembly 14. The spring 18 could also be plastic with armor or some other suitable material. The spring 18 provides the desirable amount of flexibility to permit the video camera head 16 to negotiate tight turns in a pipe P being internally inspected. The pipe P is usually buried in the ground and typically includes at least one turn. Two stainless steel aircraft cables 19 or other suitable connecting hardware attach the video camera head 16 to the termination assembly 14. The connection hardware extends longitudinally within the spring 18 and limits its extension. This facilitates removal of the video camera head 16 from the pipe P if it gets stuck.

Figure 3:
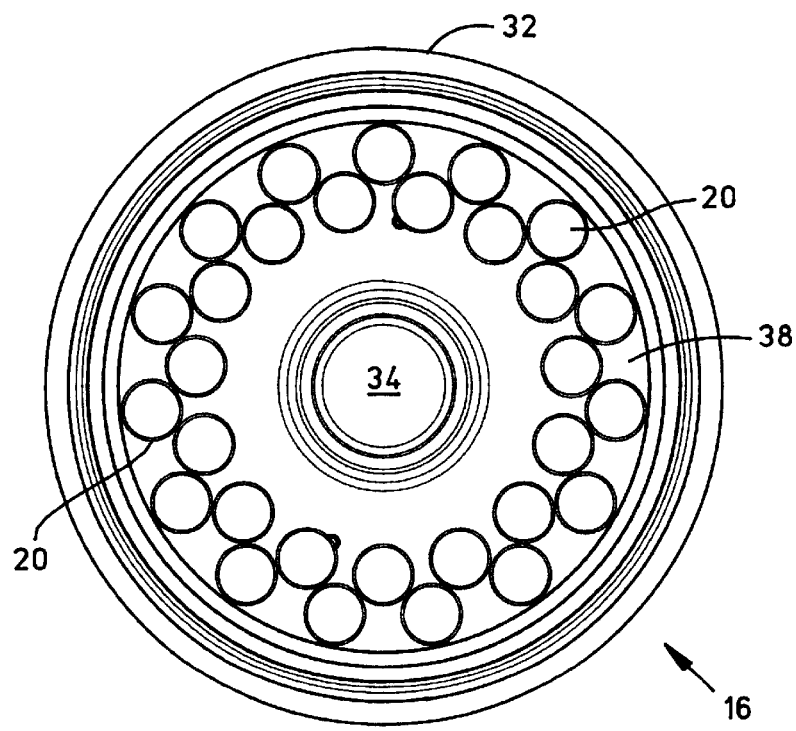
FIG. 3 is a front end elevation view of the video camera head taken from the left side of FIG. 2.

The video camera head 16 is preferably dimensioned for insertion into pipes having internal diameters as small as two inches. With advancements in video camera miniaturization, the video camera head 16 can be designed to fit within pipes having internal diameters of one inch or less. A light source is mounted in the forward end of the video camera head 16 comprising thirty white LEDs 20 (FIG. 3). This large number of LEDs provides sufficient illumination for the color video camera 17. In the particular application described herein, the scene that is illuminated by the LEDs 20 is the interior of the pipe P, including its interior walls and any objects or debris within the pipe. A pluality of red LEDs could be used in connection with red-spectrum sensitive CCDs used in black and white camera systems. In some applications infrared LEDs may be suitable. The video camera head 16 preferably has a fixed focus lens group consisting of lens elements 22a, 22b and 22c (FIG. 2) that provide a wide viewing angle with substantial depth of field, thereby eliminating the need for remote focusing in most applications. Preferably the video camera head 16 is constructed so that it is waterproof to a depth of at least three hundred and thirty feet and is capable of withstanding pressures of at least one hundred and fifty pounds per square inch (PSI).

Optionally deformable plastic fins 24 (FIG. 1) extend radially from the exterior of the video camera head 16 to centrally position the camera head within the pipe P. The push cable 12 may extend several hundred feet within the pipe P between the termination assembly 14 and a push reel 26. The push reel 26 preferably comprises a plastic annular body roughly similar in shape and size to an automobile tire. The push cable 12 is wound into continuous circular coils or turns inside the push reel 26. Due to its resilience, the coils of the push cable 12 push radially outwardly and are restrained by the annular cylindrical wall of the push reel 26. The push reel 26 is manually rotatable about a horizontal axis to pay out the push cable 12 from a circular central opening in the push reel 26. This forces the video camera head 16 down the pipe P. The push cable 12 must be pulled back out of the pipe P and pushed back inside the push reel 26 to withdraw the camera head 16.

A radio frequency ("RF") transmitter 27 (FIG. 1) can be mounted inside the coil spring 18 and powered via the push cable 12. The RF transmitter 27 emits electromagnetic signals that can be detected by proximity locating equipment so that the location of the camera head can be tracked. However, accurate location of the video camera head 16 with this technique may not be as accurate as desired or may be difficult where radio reception is poor. Therefore, the amount and direction of rotation of the push reel 26 are preferably sensed by an IR module M mounted on a stationary frame (not shown) that supports the push reel 26. The video signal transmitted over the push cable 12 passes through a slip ring coupling within the push reel 26. The video signal from the video camera 17 and a distance signal generated by the module M are processed by an electronic circuit 28. Real time video images of the interior of the pipe P are shown on a display 30 with overlaid alphanumeric distance, time and date information, all of which are recorded on a video recorder ("VCR") or other recording device such as a magnetic or optical disk drive.

It is important for the video pipe inspection system 10 to be able to accurately measure the amount of push cable 12 that has been payed out or wound back to the push reel 26. This allows breakages or blockages in the pipe P to be accurately located so that defective segment of pipe can be excavated and repaired or cleared with a snake, for example. Further details of the manner in which the module M (FIG. 1) uses infrared radiation to detect the amount and direction of rotation of the push reel 26 and the manner in which electronically determined distance information can be displayed along with the images of the interior of the pipe are disclosed in U.S. patent application Ser. No. 09/348,517 filed Jul. 7, 1999 entitled "Video Pipe Inspection Distance Measuring System" which issued as U.S. Pat. No. 6,545,704 on Apr. 8, 2003, naming Mark S. Olsson et al. as co-inventors, the entire disclosure of which is hereby incorporated by reference. Said patent is also assigned to DeepSea Power and Light.

Figure 2:
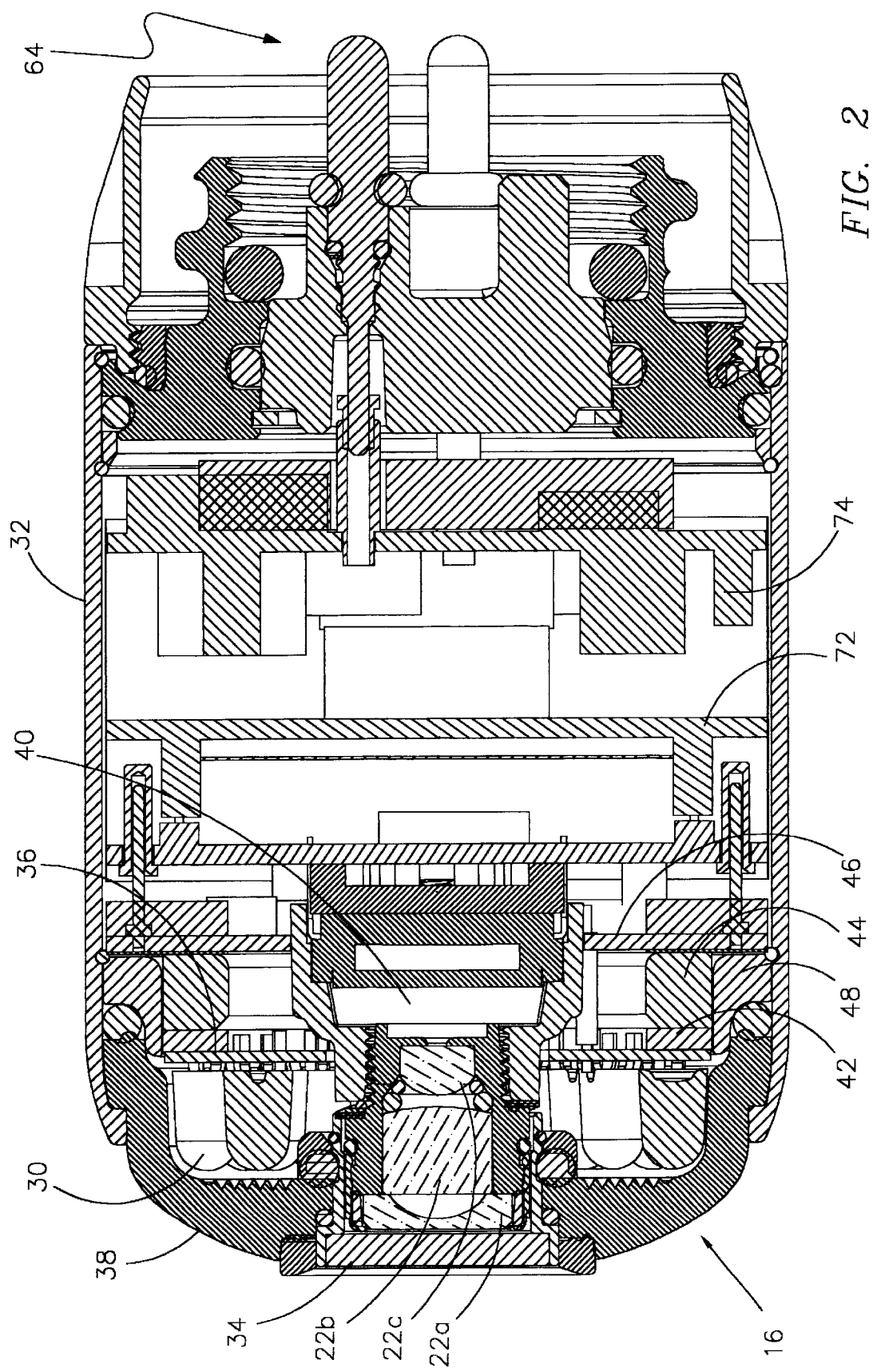
FIG. 2 is an enlarged longitudinal cross-section of the preferred embodiment of the video camera head of the present invention.

Details of the video camera head 16 are illustrated in FIGS. 2 and 3. The head 16 includes a rugged cylindrical hollow housing 32. The housing 32 of the video camera head 16 may be made of Aluminum, Titanium, stainless steel, plastic or any other durable material. The lens elements 22a, 22b and 22c are supported in a forward end of the housing 32 behind a protective window 34 preferably made of sapphire crystal or other scratch resistant transparent material. The thirty white LEDs 20 are mounted to a printed circuit board ("PCB") 36 mounted in the forward end of the housing 32 so that the LEDs 20 are circumferentially spaced about the lens elements 22a, 22b and 22c as best seen in FIG. 3. Referring to FIG. 2, a transparent plastic dome or shield 38 protects the LEDs 20 from the outside environment and seals the space between the window 34 and the forward end of the metal housing 32. When the LEDs 20 are energized by a suitable drive signal, the visible light generated by the LEDs 20 is transmitted through the dome 38 to illuminate the interior of the pipe P. Light reflected back to the video camera head 16 passes through the window 34 and lens elements 22a, 22b and 22c to an image sensing device in the form of a CCD 40. The CCD 40 has a large number of color filter elements associated therewith so that individual photosensitive elements generate color and luminance signals for a large number of pixels. The analog outputs of these photosensitive elements are repetitively swept or flushed in a predetermined sequence and processed in a well known manner to create NTSC or other standard format color video signals that are conveyed over the push cable 12. A smaller video camera head could be constructed using a video camera having an image sensing device in the form of a CMOS light sensing device.

Referring still to FIG. 2, a compliant heat sink ring 42 contacts a rear periphery of the PCB 36 and a brass heat sink ring 44. The heat sink ring 42 is preferably made of a thermally conductive polymer material such as that sold under the trademark SARCON. The heat sink ring 44 is sandwiched between the heat sink ring 42 and an LED regulator PCB 46 that surrounds the structure that centrally supports the CCD 40 within the metal housing 32 behind the lens elements 22a, 22b and 22c. A metal support ring 48 surrounds and contacts the rings 42 and 44. The metal support ring 48 is in contact with the interior of the housing 32. The heat generated by the thirty LEDs 20 is substantial and can adversely impact the signal-to-noise ratio in the output signals from the CCD 40. The rings 42, 44 and 48 provide a thermal flow path to the outer cylindrical metal housing 32 of the video camera head 16 to allow for dissipation of excess heat to limit the flow of this heat to the CCD 40. The amount of heat generated by the LEDs 20 that can be dissipated via this thermal flow path depends upon various factors, but is primarily dependent upon whether the video camera head 16 is submerged in liquid within the pipe or instead is surrounded by air, whether the pipe is metal, the temperature of the liquid or air, and so forth. As explained above, it is desirable to maximize the amount of incident light projected by the LEDs 20 in front of the camera but this also maximizes the heat dissipated by the LEDs 20.

Figure 4:
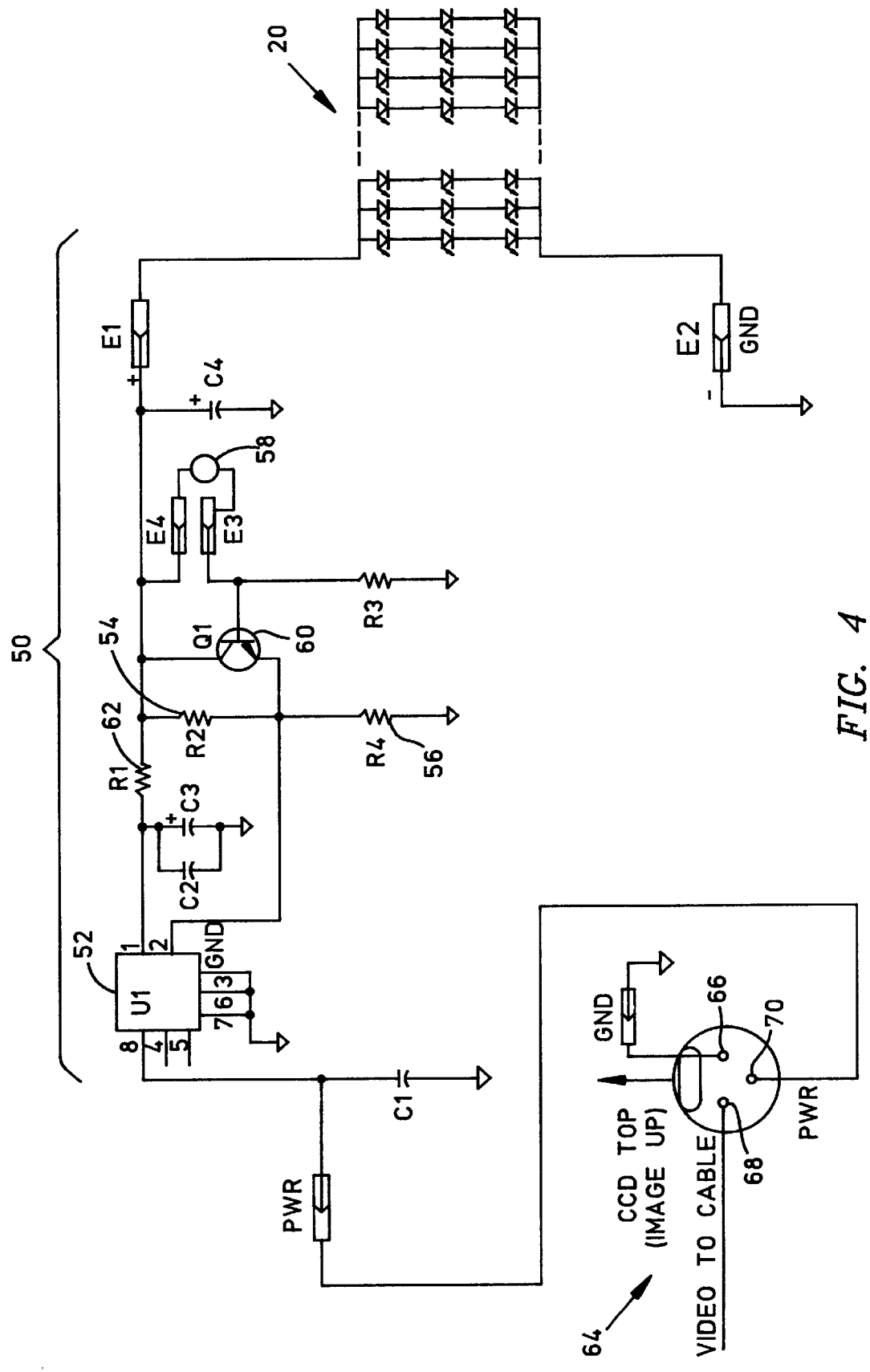
FIG. 4 is a schematic illustration of the drive circuit that controls the level of power dissipated by the LEDs of the video camera head of FIGS. 2 and 3.

As conditions within the pipe change, the drive signal to the LEDs 20 is automatically adjusted to maximize the illumination without unacceptably degrading the video output signal. In accordance with the present invention, a drive circuit 50 illustrated in FIG. 4 is connected to the LEDs 20 for driving the LEDs with a predetermined electrical drive signal. The drive circuit 50 includes a feedback loop for controlling the level of power dissipated by the LEDs 20 in order to ensure that the operating temperature of the CCD 40 does not exceed the predetermined maximum operating temperature. Except for its temperature sensor, the principal components of the drive circuit 50 are mounted on the PCB 46. As explained hereafter, the temperature sensor is mechanically mounted in the LED PCB 36 for sensing a temperature adjacent the LEDs 20 but is electrically connected to the drive circuit 50 mounted on the adjacent PCB 46.

Each of the LEDs 20 dissipates up to about one hundred and sixty mW of power, but typically dissipates about sixty mW in a steady state. The electronic circuitry of the video camera 17 mounted within the video camera head 16 typically dissipate about one and one-half mW power compared to approximately eight watts of power for all the LEDs 20 combined. This inevitably leads to excessive heat around the proximity of the CCD 40. At approximately one hundred and sixty degrees F. the noise in the output signal from the video camera 17 becomes excessive. In general, thermal noise voltage increases as the square root of the temperature increase. If the CCD 40 is subjected to a temperature higher than a predetermined maximum operating temperature for too long, it can be damaged and its performance permanently degraded.

Referring to FIG. 4, the drive circuit 50 includes an integrated circuit ("IC") voltage regulator 52 that produces a constant output supply voltage signal that energizes the LEDs 20. One suitable commercially available IC regulator is the LT 1129 manufactured by Linear Technologies. The drive circuit 50 could instead be designed to use a current regulator. Either the voltage regulator or the current regulator could be linear or switching. Pulse width modulation could be utilized.

Resistors 54 and 56 (FIG. 4) form a voltage feedback loop to the regulator 52 which it uses to sense the voltage of the drive signal to the LEDs 20. One lead of a temperature sensor in the form of a thermistor 58 is coupled to the base of a bi-polar transistor 60 while the other lead of the thermistor 58 is connected to the collector of the transistor 60 and through a resistor 62 to the regulator 52. The thermistor 58 is mounted on the rear side of the LED mounting PCB 36. The thermistor 58 is well adapted for this type of temperature feedback control circuit because of its non-linear (essentially negative exponential) resistance versus temperature characteristics. It provides a large resistance change for a relative narrow range of temperature change. When the temperature of the thermistor 58 is below the predetermined maximum operating temperature of the CCD 40, the transistor 60 is OFF and does not affect the feedback loop. As the temperature of the thermistor 58 approaches the predetermined maximum temperature, the voltage at the base of the transistor 60 rises to the point where the transistor 60 is turned ON. This decreases the output of the regulator 52 until the temperature of the thermistor 58 decreases a predetermined amount. The light output of the LEDs 20 thus varies from a predetermined maximum to a low enough level to achieve an equilibrium condition between the heat dissipated by the LEDs 20 and the heat lost to the environment through the camera housing 32.

As illustrated in FIGS. 2 and 4, the video camera head 16 includes a socket assembly 64 that provides ground, video output signal and power pins 66, 68 and 70, respectively. The power pin 70 is connected to the regulator 52. The circuitry of the video camera 17 is principally mounted on PCBs 72 and 74.

In addition to a video camera head with thermal feedback control, our invention also provides a method of providing improved video images of the inside of a pipe. The images are improved in that they have better resolution and color owing to the fact that the illumination provided by the LEDs is maximized without inducing undesirable noise in the video output signal due to excessive heat exposure of the CCD. The method involves mounting a video camera 17 inside a housing 32 for generating video signals of an image of an interior of a pipe P, the camera 17 having an image sensing device 40 with a predetermined maximum operating temperature. The method further involves operatively connecting the housing 32 and the camera 17, via termination assembly 14 and socket assembly 64, to the distal end of a video push cable 12 and pushing the housing 32 and video camera 17 down the interior of the pipe P by paying out the video push cable 12. The method further involves driving at least one light emitting diode 20 mounted in a front end of the housing 32 with a predetermined electrical drive signal to illuminate the interior of the pipe P and controlling the level of power dissipated by the light emitting diode 20 in order to ensure that the operating temperature of the image sensing device 40 of the video camera 17 does not exceed the predetermined maximum operating temperature. Finally, the method involves displaying on a display 30 images of the interior of the pipe P generated from a video output signal conveyed from the video camera 17 over the video push cable 12.

While we have described a preferred embodiment of our video camera head with thermal feedback lighting control, and a method of providing improved video images of the inside of a pipe, it should be apparent to those skilled in the art that our invention may be modified in both arrangement and detail. For example, the utility of our invention is not limited to a video pipe inspection system. Temperature sensing could be based on the change in LED forward voltage. The video camera head could be constructed with a side looking video camera. The camera could rotate for both forward and side looking and LEDs could be mounted for side illumination and switched OFF when the camera is forward looking. Therefore the protection afforded our invention should only be limited in accordance with the following claims.

We claim:

1. A video camera head for pipe inspection, comprising:
    a camera housing having a hollow interior;
    a video camera mounted inside the housing for generating video signals of an image of an interior of a pipe, the camera having an image sensing device with a predetermined maximum operating temperature;
    means for operatively coupling a video push cable to the camera housing and the video camera;
    at least one light emitting diode mounted in the housing for illuminating the interior of the pipe; and
    a drive circuit connected to the light emitting diode for driving the light emitting diode with a predetermined electrical drive signal including a feedback loop for controlling the level of power dissipated by the light emitting diode in order to ensure that the operating temperature of the image sensing device does not exceed the predetermined maximum operating temperature.
2. The video camera head of claim 1 wherein the image sensing device is a charge coupled device.
3. The video camera head of claim 1 wherein there are a plurality of light emitting diodes mounted in a forward end of the camera and connected to the drive circuit.
4. The video camera head of claim 3 wherein the plurality of light emitting diodes are mounted in circumferential relationship around a window mounted in the forward end of the camera housing.
5. The video camera head of claim 1 wherein the light emitting diode is mounted in a circuit board mounted in the camera housing.
6. The video camera head of claim 5 wherein the circuit board is thermally coupled to a heat sink mounted in the camera housing.
7. The video camera head of claim 1 wherein the feedback loop of the drive circuit includes a temperature sensor.
8. The video camera head of claim 1 wherein the feedback loop of the drive circuit includes a temperature sensor mounted in a circuit board to which light emitting diode is mounted.
9. The video camera head of claim 1 wherein the drive circuit adjusts a supply voltage signal to the light emitting diode based on sensed temperature to achieve substantial equilibrium between heat generated by the light emitting diode and heat lost to the environment through the camera housing.
10. The video camera head of claim 1 wherein the camera housing is made of metal.
11. A method of providing video images of the inside of a pipe, comprising the steps of:
    mounting a video camera inside a housing for generating video signals of an image of an interior of a pipe, the camera having an image sensing device with a predetermined maximum operating temperature;
    operatively connecting the housing and the camera to the distal end of a video push cable;
    pushing the housing and video camera down the interior of the pipe by paying out the video push cable;
    driving at least one light emitting diode mounted on the housing with a predetermined electrical drive signal to illuminate the interior of the pipe;
    controlling the level of power dissipated by the light emitting diode in order to ensure that the operating temperature of the image sensing device of the video camera does not exceed the predetermined maximum operating temperature; and
    displaying images of the interior of the pipe generated from a video output signal conveyed from the video camera over the video push cable.
12. The method of claim 11 and further comprising the steps of measuring the amount of the video push cable within the pipe and displaying distance information along with the images of the interior of the pipe.
13. The method of claim 11 wherein the level of power dissipated by the light emitting diode is controlled in order to achieve substantial equilibrium between heat generated by the light emitting diode and heat lost to the environment through the camera housing.
14. The method of claim 11 wherein the level of power dissipated by the light emitting diode is controlled using a feedback loop including a temperature sensor.
15. The method of claim 11 wherein the temperature sensor is mounted adjacent the light emitting diode.

* * * * *